US009131769B2

(12) United States Patent
Obernesser et al.

(10) Patent No.: US 9,131,769 B2
(45) Date of Patent: Sep. 15, 2015

(54) OPEN BRIDGE RACK

(71) Applicant: FMR LLC, Boston, MA (US)

(72) Inventors: Brian Obernesser, Raleigh, NC (US); Dale B Clark, Jr., Placentia, CA (US)

(73) Assignee: FMR LLC, Boston, MA (US)

( * ) Notice: Subject to any disclaimer, the term of this patent is extended or adjusted under 35 U.S.C. 154(b) by 0 days.

(21) Appl. No.: 14/502,674

(22) Filed: Sep. 30, 2014

(65) Prior Publication Data

US 2015/0090679 A1 Apr. 2, 2015

Related U.S. Application Data

(60) Provisional application No. 61/884,853, filed on Sep. 30, 2013.

(51) Int. Cl.
*A47G 29/00* (2006.01)
*A47B 46/00* (2006.01)
*A47B 47/00* (2006.01)
*A47B 96/14* (2006.01)
*H05K 7/14* (2006.01)

(52) U.S. Cl.
CPC ............. *A47B 46/00* (2013.01); *A47B 47/0083* (2013.01); *A47B 96/1416* (2013.01); *H05K 7/1488* (2013.01)

(58) Field of Classification Search
CPC ........................................................ H02B 1/014
USPC .......... 312/265.1, 265.2, 265.3, 265.4, 223.1; 211/26
See application file for complete search history.

(56) References Cited

U.S. PATENT DOCUMENTS

| | | | | |
|---|---|---|---|---|
| 5,571,256 | A * | 11/1996 | Good et al. ...................... | 211/26 |
| 6,497,465 | B1 * | 12/2002 | Baker et al. ................. | 312/334.4 |
| 6,578,939 | B1 | 6/2003 | Mayer | |
| 6,655,533 | B2 | 12/2003 | Guebre-Tsadik | |
| 6,808,240 | B2 * | 10/2004 | Altena ........................ | 312/265.4 |
| 6,974,037 | B2 * | 12/2005 | Haney ............................ | 211/26 |
| 7,780,253 | B1 * | 8/2010 | Lu .............................. | 312/334.4 |
| 7,934,607 | B2 | 5/2011 | Henderson et al. | |
| 8,356,718 | B2 | 1/2013 | Yang | |
| 2001/0040142 | A1 * | 11/2001 | Haney .......................... | 211/183 |
| 2003/0034717 | A1 * | 2/2003 | Yao ............................ | 312/223.1 |
| 2004/0079712 | A1 * | 4/2004 | Mayer ............................ | 211/26 |
| 2004/0159618 | A1 * | 8/2004 | Nguyen et al. ................. | 211/26 |
| 2008/0198536 | A1 * | 8/2008 | Ewing et al. .................. | 361/622 |
| 2010/0110621 | A1 * | 5/2010 | Dunn et al. .............. | 361/679.01 |
| 2011/0304244 | A1 * | 12/2011 | Cottuli et al. .............. | 312/223.1 |
| 2012/0018389 | A1 * | 1/2012 | Fan ................................ | 211/26 |
| 2013/0091689 | A1 | 4/2013 | Mimlitch, III et al. | |

* cited by examiner

*Primary Examiner* — Matthew Ing
(74) *Attorney, Agent, or Firm* — Proskauer Rose LLP

(57) ABSTRACT

An equipment rack includes a frame, a first pair of mounting rails and a second pair of mounting rails. Each pair of mounting rails includes a front mounting rail and a rear mounting rail and the front and rear mounting rails each include a first planar surface defining in part a first equipment-mounting interface when the front and rear mounting rails are coupled to the frame through a second planar surface of each of the front and rear mounting rails in a first configuration. The front and rear mounting rails each further include a third planar surface and a fourth planar surface defining in part a second equipment-mounting interface when the front and the rear mounting rails are coupled to the frame through the first planar surface in a second configuration. The first and second equipment-mounting interfaces can be defined by an equipment rack standard.

30 Claims, 8 Drawing Sheets

OPEN BRIDGE RACK

RELATED APPLICATIONS

This application claims priority to U.S. Provisional Patent Application No. 61/884,853, filed Sep. 30, 2013, the entirety of which is incorporated herein by reference.

FIELD OF THE INVENTION

The subject matter of this application relates generally to equipment racks, and more particularly to Information Technology ("IT") equipment racks that can be configured to support multiple equipment rack standards.

BACKGROUND

Equipment racks are used extensively for mounting Information Technology ("IT") equipment. Equipment racks typically include a frame and/or an enclosure with two or four vertical posts provided to which IT equipment is mounted. Several formal standards exist which dictate the specifications of particular equipment racks. For example, equipment rack standards commonly specify an incremental equipment height value or Rack Unit ("RU"), a vertical mounting hole spacing, a rack equipment opening width, and a width value for the front panel of the IT equipment that will be mounted in the rack.

One of the most prevalent standards for equipment racks is Electronic Industries Alliance EIA-310 ("EIA standard," or "EIA-310"), which specifies a rack that has a RU of 1.75" (44.45 mm) and can accommodate IT equipment with a 19" (482.6 mm) front panel width. Each piece of IT equipment mounted in EIA-compliant racks typically includes two or more live AC to DC power converters to provide redundancy in the event of a component failure. The redundant power converters generate a significant amount of heat and have a low overall operating efficiency. Furthermore, the 19" front panel width specification of the EIA standard limits the possible placement and orientation of individual electronic components within IT equipment. As a result, complicated airflow management schemes are required to maintain safe operating temperatures for all rack-mounted IT equipment.

The Open Compute Project ("OCP") is an initiative to share data center product designs. The OCP provides the Open Rack Standard which includes specifications for an equipment rack, known as the Open Rack. The Open Rack under the OCP standard can have similar depth and outer width specifications as an EIA-compliant rack; however, the OCP-compliant rack provides a 538 mm (approximately 21-inch) opening for mounting wider IT equipment. The OCP standard also specifies a Rack Unit, referred to as an "OpenU," of approximately 1.9" (48 mm). An OCP-compliant rack can also include an integrated power distribution bus system and power shelves for housing standardized power converters.

The difference in specifications between the EIA-compliant equipment rack and the OCP-compliant equipment rack make them incompatible, i.e., an OCP-compliant equipment rack cannot be used to mount IT equipment designed to be mounted in a 19" EIA-compliant rack and vice-versa.

SUMMARY OF THE INVENTION

There is a need for an equipment rack that can be used for mounting currently-owned EIA-compatible IT equipment, but can be easily configured to be used for mounting next-generation OCP-compatible equipment. One advantage of the equipment rack of the present disclosure is that it provides a single equipment rack that can bridge the gap between the standard EIA 19" rack design and the developing OCP Open Rack design, with an ability to convert from one standard to the other. Another advantage of the equipment rack of the present disclosure is that it can be easily converted from an EIA-compliant equipment rack to an OCP-compliant equipment rack without having to be physically relocated. Another advantage of the equipment rack of the present disclosure is that it provides a wider opening to mount IT equipment in the OCP configuration, and fits more IT equipment per volume. Another advantage of the equipment rack of the present disclosure is that it provides better airflow management for cooling IT equipment mounted in the equipment rack. Another advantage of the equipment rack of the present disclosure is that it can disaggregate power from the rack itself.

The invention, in one aspect, features an equipment rack including a frame, a first pair of mounting rails, and a second pair of mounting rails. Each pair of mounting rails includes a front mounting rail having a first plurality of front equipment-mounting apertures disposed substantially adjacent to an outer edge of a first planar surface of the front mounting rail. The first planar surface has a first width sized to align the first plurality of front equipment-mounting apertures at a first predefined position defining in part a first equipment-mounting interface when the front mounting rail is coupled to the frame through a second planar surface of the front mounting rail that is substantially perpendicular to the first planar surface. The front mounting rail also includes a second plurality of front equipment-mounting apertures being disposed in a third planar surface of the front mounting rail that is substantially perpendicular to the second planar surface, and a fourth planar surface of the front mounting rail surface that is substantially perpendicular to the third planar surface. The second planar surface has a second width sized to align the second plurality of front equipment-mounting apertures disposed in the third planar surface at a second predefined position defining in part a second equipment-mounting interface, and the third planar surface has a third width sized to align the second plurality of front equipment-mounting apertures disposed in the fourth planar surface at a third predefined position defining in part the second equipment-mounting interface when the front mounting rail is coupled to the frame through the first planar surface.

Each pair of mounting rails also includes a rear mounting rail including a first plurality of rear equipment-mounting apertures disposed substantially adjacent to an outer edge of a first planar surface of the rear mounting rail. The first planar surface has a fourth width sized to align the first plurality of rear equipment-mounting apertures at a fourth predefined position defining in part the first equipment-mounting interface when the rear mounting rail is coupled to the frame through a second planar surface of the rear mounting rail that is substantially perpendicular to the first planar surface. The rear mounting rail also includes a second plurality of rear equipment-mounting apertures disposed in a fourth planar surface of the rear mounting rail that is substantially perpendicular to a third planar surface of the rear mounting rail that is substantially perpendicular to the second planar surface. The second planar surface has a fifth width sized to align the third planar surface at a fifth predefined position defining in part the second equipment-mounting interface, and the third planar surface has a sixth width sized to align the second plurality of rear equipment-mounting apertures at a sixth predefined position defining in part the second equipment-mounting interface when the rear mounting rail is coupled to the frame through the first planar surface. The first equipment-mounting interface is defined by a first configuration of the first and second pairs of mounting rails. The second equipment-mounting interface is defined by a second configuration of the first and second pairs of mounting rail.

In some embodiments of the equipment rack, the first equipment-mounting interface complies with a first equipment rack standard specifying an equipment rack for mounting equipment having a first front panel width, the first front panel width being substantially 19 inches. In some embodiments of the equipment rack, the first equipment rack standard is a version of Electronic Industries Alliance 310 (EIA-310). In some embodiments of the equipment rack, the second equipment-mounting interface complies with a second equipment-mounting standard specifying an equipment rack for mounting equipment having a first enclosure width that is substantially 538 millimeters. In some embodiments of the equipment rack, the second equipment rack standard is a version of an Open Compute Project Open Rack standard.

In some embodiments of the equipment rack, the first and second pairs of mounting rails in the first configuration are rotated substantially ninety degrees about a longitudinal axis in the second configuration. In some embodiments, the first pair of mounting rails is coupled to a first side of the frame in the first configuration and the second pair of mounting rails is coupled to a second side of the frame in the first configuration. In some embodiments, the first pair of mounting rails is coupled to the second side of the frame in the second configuration and the second pair of mounting rails is coupled to the first side of the frame in the second configuration. In some embodiments, the first and second pairs of mounting rails in the first configuration are each rotated substantially one hundred eighty degrees about a horizontal axis in the second configuration. In some embodiments, the first pair of mounting rails is coupled to a first side of the frame in the second configuration and the second pair of mounting rails is coupled to a second side of the frame in the second configuration.

In some embodiments, the equipment rack further includes a plurality of wire management blocks for coupling to the frame when the first and second pairs of mounting rails are in the second configuration. Each wire management block is configured to provide a recessed channel for routing one or more wires within, and provide a first alignment surface with which to align one front mounting rail. The first alignment surface is a first predetermined distance from a vertical member of the frame adjacent to the front mounting rail. In some embodiments, the equipment rack further includes a plurality of power bus blocks for coupling to the frame when the first and second pairs of mounting rails are in the second configuration. Each power bus block is configured to provide a first power bus mounting surface for mounting power bus components in the equipment rack, and provide a second alignment surface with which to align one rear mounting rail. The second alignment surface is a second predetermined distance from a vertical member of the frame adjacent to the rear mounting rail.

The invention, in another aspect, features a kit for configuring an equipment rack that includes a frame. The kit includes a first pair of mounting rails, and a second pair of mounting rails. Each pair of mounting rails includes a front mounting rail having a first plurality of front equipment-mounting apertures disposed substantially adjacent to an outer edge of a first planar surface of the front mounting rail. The first planar surface has a first width sized to align the first plurality of front equipment-mounting apertures at a first predefined position defining in part a first equipment-mounting interface when the front mounting rail is coupled to the frame through a second planar surface of the front mounting rail that is substantially perpendicular to the first planar surface. The front mounting rail also includes a second plurality of front equipment-mounting apertures being disposed in a third planar surface of the front mounting rail that is substantially perpendicular to the second planar surface, and a fourth planar surface of the front mounting rail surface that is substantially perpendicular to the third planar surface. The second planar surface has a second width sized to align the second plurality of front equipment-mounting apertures disposed in the third planar surface at a second predefined position defining in part a second equipment-mounting interface, and the third planar surface has a third width sized to align the second plurality of front equipment-mounting apertures disposed in the fourth planar surface at a third predefined position defining in part the second equipment-mounting interface when the front mounting rail is coupled to the frame through the first planar surface.

Each pair of mounting rails also includes a rear mounting rail including a first plurality of rear equipment-mounting apertures disposed substantially adjacent to an outer edge of a first planar surface of the rear mounting rail. The first planar surface has a fourth width sized to align the first plurality of rear equipment-mounting apertures at a fourth predefined position defining in part the first equipment-mounting interface when the rear mounting rail is coupled to the frame through a second planar surface of the rear mounting rail that is substantially perpendicular to the first planar surface. The rear mounting rail also includes a second plurality of rear equipment-mounting apertures disposed in a fourth planar surface of the rear mounting rail that is substantially perpendicular to a third planar surface of the rear mounting rail that is substantially perpendicular to the second planar surface. The second planar surface has a fifth width sized to align the third planar surface at a fifth predefined position defining in part the second equipment-mounting interface, and the third planar surface has a sixth width sized to align the second plurality of rear equipment-mounting apertures at a sixth predefined position defining in part the second equipment-mounting interface when the rear mounting rail is coupled to the frame through the first planar surface. The first equipment-mounting interface is defined by a first configuration of the first and second pairs of mounting rails. The second equipment-mounting interface is defined by a second configuration of the first and second pairs of mounting rail.

In some embodiments of the kit, the first equipment-mounting interface complies with a first equipment rack standard specifying an equipment rack for mounting equipment having a first front panel width, the first front panel width being substantially 19 inches. In some embodiments, the first equipment rack standard is a version of Electronic Industries Alliance 310 (EIA-310). In some embodiments, the second equipment-mounting interface complies with a second equipment-mounting standard specifying an equipment rack for mounting equipment having a first enclosure width that is substantially 538 millimeters. In some embodiments, the second equipment rack standard is a version of an Open Compute Project Open Rack standard.

In some embodiments of the kit, the first and second pairs of mounting rails in the first configuration are rotated substantially ninety degrees about a longitudinal axis in the second configuration. In some embodiments, the first pair of mounting rails is coupled to a first side of the frame in the first configuration and the second pair of mounting rails is coupled to a second side of the frame in the first configuration. In some embodiments, the first pair of mounting rails is coupled to the second side of the frame in the second configuration and the second pair of mounting rails is coupled to the first side of the frame in the second configuration. In some embodiments, the first and second pairs of mounting rails in the first configuration are each rotated substantially one hundred eighty degrees about a horizontal axis in the second configuration. In some embodiments, the first pair of mounting rails is coupled to a first side of the frame in the second configuration and the second pair of mounting rails is coupled to a second side of the frame in the second configuration.

In some embodiments, the kit includes a plurality of wire management blocks for coupling to the frame when the first and second pairs of mounting rails are in the second configuration. Each wire management block is configured to provide a recessed channel for routing one or more wires within, and provide a first alignment surface with which to align one front mounting rail. The first alignment surface is a first predetermined distance from a vertical member of the frame adjacent to the front mounting rail. In some embodiments, the equipment rack further includes a plurality of power bus blocks for coupling to the frame when the first and second pairs of mounting rails are in the second configuration. Each power bus block is configured to provide a first power bus mounting surface for mounting power bus components in the equipment rack, and provide a second alignment surface with which to align one rear mounting rail. The second alignment surface is a second predetermined distance from a vertical member of the frame adjacent to the rear mounting rail The invention, in another aspect, features a method for configuring an equipment rack including a frame. A first pair of mounting rails and a second pair of mounting rails are coupled to the frame in a first configuration defining a first equipment-mounting interface. The first pair of mounting rails is coupled to a first side of the frame, and the second pair of mounting rails is coupled to a second side of the frame. Each pair of mounting rails includes a front mounting rail and a rear mounting rail, and the front and rear mounting rails each include a first planar surface defining in part the first equipment-mounting interface when the front and rear mounting rails are coupled to the frame through a second planar surface of each of the front and rear mounting rails.

The first and second pairs of mounting rails are decoupled from the frame. The first and second pairs of mounting rails are rotated substantially ninety degrees about a longitudinal axis, and coupled to the frame in a second configuration defining a second equipment-mounting interface.

The first and second pairs of mounting rails are coupled to the frame in a second configuration defining a second equipment-mounting interface. The front and rear mounting rails of the first and second pairs of mounting rails each further include a third planar surface and a fourth planar surface defining in part the second equipment-mounting interface when the front and the rear mounting rails are coupled to the frame through the first planar surface of each of the front and rear mounting rails.

In some embodiments, the step of coupling the first and second pairs of mounting rails to the frame in the second configuration further includes aligning the first pair of mounting rails to the second side of the frame, and aligning the second pair of mounting rails to the first side of the frame. In some embodiments, the step of coupling the first and second pairs of mounting rails to the frame in the second configuration further includes rotating each mounting rail substantially one hundred eighty degrees about a horizontal axis, aligning the first pair of mounting rails to the first side of the frame, and aligning the second pair of mounting rails to the second side of the frame.

In some embodiments, the method further includes coupling a plurality of wire management blocks to the frame. Each wire management block is configured to provide a recessed channel for routing one or more wires within, and provide a first alignment surface with which to align one front mounting rail in the second configuration. The first alignment surface is a first predetermined distance from a vertical member of the frame adjacent to the front mounting rail. In some embodiments, the method further includes coupling a plurality of power bus blocks to the frame. Each power bus block is configured to provide a first power bus mounting surface for mounting power bus components to the equipment rack, and provide a second alignment surface with which to align one rear mounting rail in the second configuration. The second alignment surface is a second predetermined distance from a vertical member of the frame adjacent to the rear mounting rail.

In some embodiments, the step of coupling the first and second pairs of mounting rails to the frame in the second configuration further includes aligning the second planar surfaces of the front mounting rails adjacent to the first alignment surfaces of the plurality of wire management blocks, and aligning the second planar surfaces of the rear mounting rails adjacent to the second alignment surfaces of the plurality of power bus blocks.

In some embodiments, rotating the first and second pairs of mounting rails substantially ninety degrees about a longitudinal axis includes rotating the front mounting rail of the first pair of mounting rails and the rear mounting rail of the second pair of mounting rails in a clockwise direction relative to the longitudinal axis, and rotating the front mounting rail of the second pair of mounting rails and the rear mounting rail of the first pair of mounting rails in a counterclockwise direction relative to the longitudinal axis.

Other aspects and advantages of the embodiments described herein will become apparent from the following detailed description, taken in conjunction with the accompanying drawings.

BRIEF DESCRIPTION OF THE DRAWINGS

The advantages of the embodiments described herein, together with further advantages, may be better understood by referring to the following description taken in conjunction with the accompanying drawings. The drawings are not necessarily to scale; emphasis is instead generally being placed upon illustrating the principles of the embodiments.

FIGS. 6A, 6B-1, and 6B-2 are a series of diagrams corresponding to a method for configuring an equipment rack according to embodiments of this disclosure.

DETAILED DESCRIPTION

Figure 1:
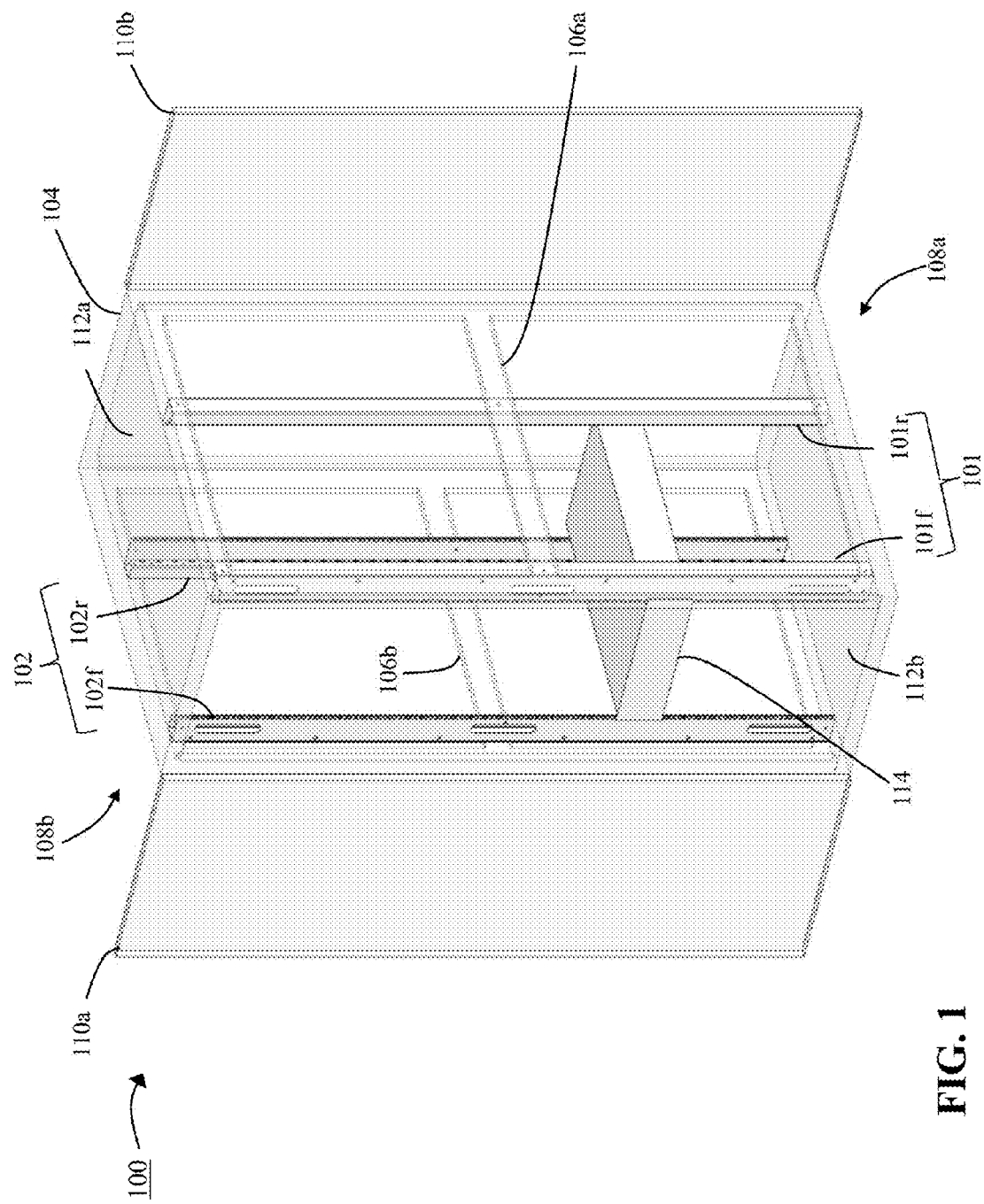
FIG. 1 is a perspective view of an EIA-compliant equipment rack including IT equipment-mounting rails in accordance with an embodiment of this disclosure.

FIG. 1 shows a perspective view of an EIA-compliant equipment rack 100 in accordance with embodiments of this disclosure. The overall dimensions of rack 100 can vary according to vendor or customer preferences. In some embodiments, the overall dimensions of rack 100 are 28" wide×48" deep×83" high. Rack 100 includes a frame 104, comprising vertical and horizontal members that are coupled together. The frame 104 can include an upper section and a lower section, each comprised of four horizontal beams coupled together and forming a rectangle. The frame 104 can further include four vertical supports with each end coupled to a corresponding corner of the upper and lower sections. As shown in FIG. 1, the frame 104 includes a first horizontal strut 106a coupled between the vertical supports on a first side 108a (e.g., right side) of the frame 104, and a second horizontal strut 106b coupled between the vertical supports on a second side 108b (e.g., left side) of the frame 104. In some embodiments, the frame 104 is formed without horizontal struts 106a and 106b. In some embodiments, rail-coupling apertures (e.g., slots, round holes, threaded holes, square holes, and rectangular holes) are disposed at fixed intervals along the vertical and horizontal members making up the frame 104 for coupling mounting rails and other components to the frame 104. It should be appreciated that equipment rack frames in any number of configurations with additional features (e.g., leveling feet, floor-mounting flanges, etc.) can be used without departing from the scope of the invention. Frame 104 is drawn semi-transparent in FIG. 1 and other figures of the disclosure so as to not obscure other features and components described herein.

As shown in FIG. 1, rack 100 further includes a front door 110a, and a rear door 110b, however, doors 110a and 110b are optional components and are not required for practicing the disclosed invention. Similarly, in some embodiments rack 100 optionally includes a top wall 112a and a bottom wall 112b, and/or left and right sidewalls (not shown).

As shown in FIG. 1, rack 100 includes a first pair of IT equipment-mounting rails 101 comprising a front mounting rail 101f and a rear mounting rail 101r, and a second pair of IT equipment-mounting rails 102 comprising a front mounting rail 102f and a rear mounting rail 102r. The rails 101 and 102 are each coupled to frame 104 in an orientation and position (e.g., in a first configuration) such that rack 100 provides a first equipment-mounting interface 114. The first equipment-mounting interface 114 is defined in part by features and dimensions of each of the mounting rails 101 and 102 and provides an interface for mounting IT equipment and other rack-mountable equipment. The particular dimensions and mounting features of the interface 114 can be specified by an equipment rack standard. In one embodiment, the interface 114 is defined by a version of EIA-310. For example, the interface 114 can include IT equipment-mounting apertures (also referred to as equipment-mounting apertures) that are grouped as repeated patterns of holes within a Rack Unit ("RU" or "U") (e.g., three apertures per 1.750" of vertical linear distance) with a defined center-to-center vertical hole spacing of the apertures within an RU (e.g., 0.625") and between adjacent RUs (e.g., 0.5"). The interface 114 can include a defined horizontal center-to-center hole spacing (e.g., 18.312") between IT equipment-mounting apertures of the front mounting rails of each pair of mounting rails, and a horizontal center-to-center hole spacing (e.g., 18.312") between IT equipment-mounting apertures of the rear mounting rails of each pair of mounting rails. The interface 114 can further include a defined opening (e.g., 17.72") between an outer edge of a surface of the front mounting rails of each pair of mounting rails and a defined front panel width (e.g., 19") for the IT equipment that can be mounted in the rack 100. As represented in FIG. 1, the vertical height of the interface 114 encompasses 3U, however, it should be understood that the interface 114 can encompass as few as 1U or 2U, or alternatively 4U or more depending on the height of the IT equipment that is being mounted in rack 100. The features and dimensions of the interface 114 are provided in repeated 1U intervals along substantially the entire length of the rails 101 and 102 when the rails 101 and 102 are coupled to the frame 104 in the first configuration. In some embodiments the interface 114 can provide up to 48U of mounting interface for IT equipment.

Figure 2:
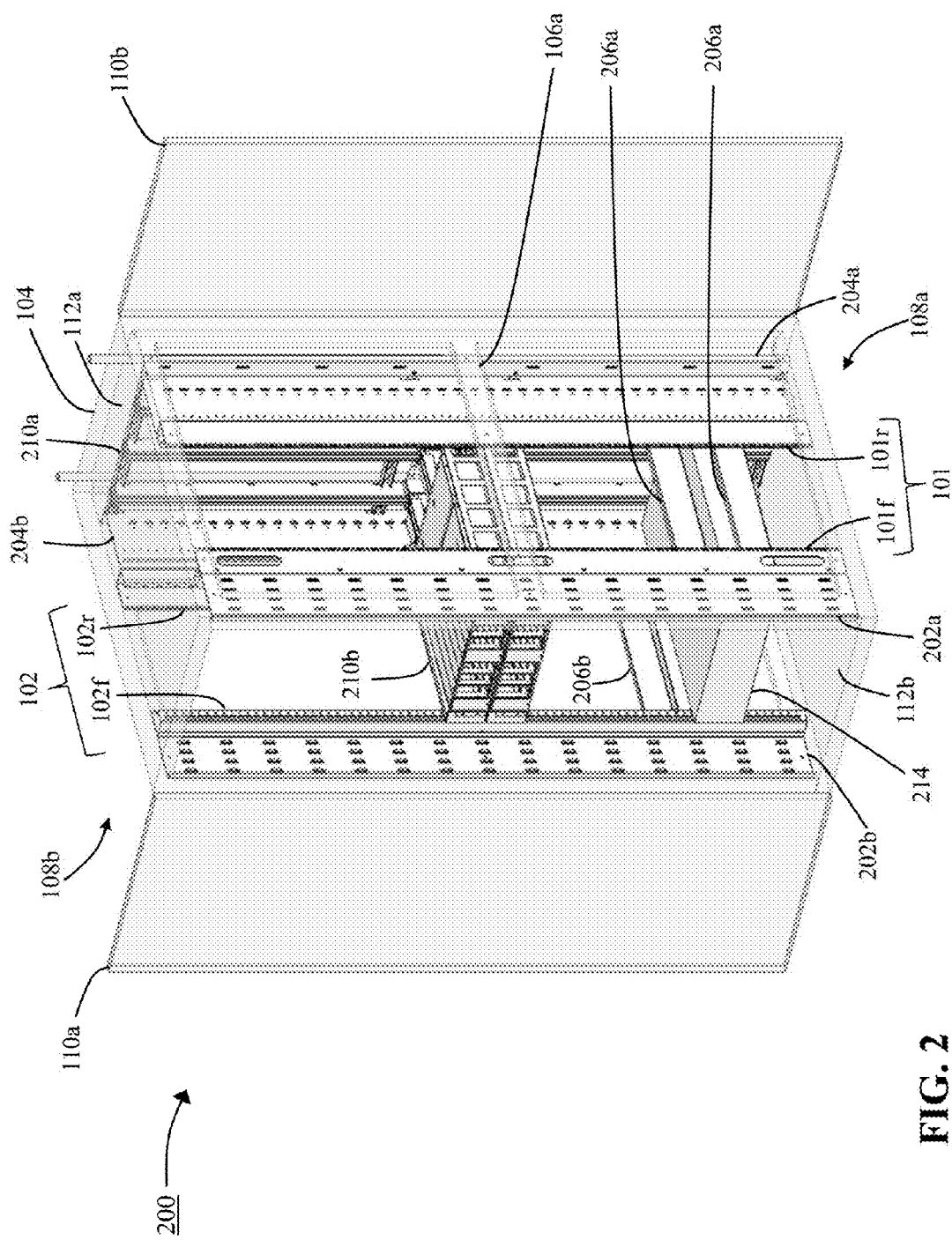
FIG. 2 is a perspective view of an OCP-compliant equipment rack including IT equipment-mounting rails in accordance with an embodiment of this disclosure.

FIG. 2 shows a perspective view of an OCP-compliant equipment rack 200 in accordance with embodiments of this disclosure. Rack 200 can include many of the same components as EIA-compliant equipment rack 100. For example, rack 200 can include a frame 104, comprising vertical and horizontal members coupled together as described above. Rack 200 can optionally include a front door 103, and a rear door 104. In some embodiments, the overall dimensions of OCP-compliant equipment rack 200 are 28" wide×48" deep× 83" high. In some embodiments, rack 200 optionally includes a top wall 112a and a bottom wall 112b, and/or left and right sidewalls (not shown).

As shown in FIG. 2, rack 200 includes a first pair of IT equipment-mounting rails 101 comprising a front mounting rail 101f and a rear mounting rail 101r, and a second pair of IT equipment-mounting rails 102 comprising a front mounting rail 102f and a rear mounting rail 102r, which are each coupled to frame 104 in an orientation and position (e.g., in a second configuration) such that rack 200 provides a second equipment-mounting interface 214. The second equipment-mounting interface 214 is defined in part by features and dimensions of each of the mounting rails 101 and 102 and provides an interface for mounting and securing IT equipment and other rack-mountable equipment. The particular dimensions and mounting features of the interface 214 can be specified by an equipment rack standard. In one embodiment, the interface 214 is defined by a version of the OCP Open Rack. For example, the interface 214 can include IT equipment-mounting apertures (also referred to as equipment-mounting apertures) disposed in each of the rails 101 and 102 that are grouped as a repeated alternating pattern of holes and/or lanced openings within a defined Rack Unit ("OpenU") (e.g., rectangular holes repeated every 48 mm of vertical linear distance and offset lanced openings repeated every 48 mm of vertical linear distance). The interface 214 can further include a defined horizontal linear distance (e.g., 521 mm) from the IT equipment-mounting apertures of each front rail (101f, 102f) to the IT equipment-mounting apertures of the respective rear mounting rail (101r, 102r). The interface 214 can include additional IT equipment-mounting apertures in the front mounting rails 101f and 102f that are grouped as a repeated pattern of rectangular holes and adjacent lanced openings within an OpenU (e.g., a rectangular hole and adjacent lanced opening repeated every 48 mm of vertical linear distance), or half of an OpenU (e.g., a rectangular hole and adjacent lanced opening repeated every 24 mm of vertical linear distance). The interface 214 can further include a defined distance (e.g., 538 mm) between the front mounting rails 101f and 102f of each pair of mounting rails 101 and 102, and a defined distance (e.g., 538 mm) between the rear mounting rails 101r and 102r of each pair of mounting rails 101 and 102 which collectively define the maximum enclosure width of the IT equipment that can be mounted in rack 200. As represented in FIG. 2, the vertical height of the interface 214 encompasses 3 OpenU, however, it should be understood that the interface 214 can encompass as few as 1 OpenU or 2 OpenU, or alternatively 4 OpenU or more depending on the height of the IT equipment that is being mounted in rack 200. The features and dimensions of the interface 214 are repeated in 1 OpenU intervals along substantially the entire length of the rails 101 and 102 when the rails 101 and 102 are coupled to the frame 104 in the second configuration.

Rack 200 further includes two wire management blocks 202a and 202b (collectively referred to as blocks 202), which are also coupled to frame 104. In some embodiments, the blocks 202 are formed using stamped sheet metal (e.g., aluminum, steel) that is bent into a C-shaped channel that can be used for neatly routing and retaining the data cables attached to IT equipment mounted in rack 200. For example, the blocks 202 can provide a recessed channel on the sides of the rack 200 in which to route cables so that the IT equipment will not disconnect or damage the cables when it is added or removed. The blocks 202 can further include flanges or lanced openings formed in the channel for retaining the data cables with retention components (e.g., zip ties, Velcro straps). The blocks 202 can further be used as positioning guides when installing the front mounting rails 101f and 102f. For example, a surface of blocks 202 can be used as a reference when aligning the front mounting rails 101f and 102f to the frame 104 in the second configuration. In some embodiments, the blocks 202 are identical components. In some embodiments, the blocks 202 are uniquely designed components that are mirror-images of each other. In some embodiments, the features and dimensions of the blocks 202 are defined by an equipment rack standard (e.g., a version of the OCP Open Rack Standard).

Rack 200 further includes two power bus blocks 204a and 204b (collectively referred to as blocks 204), which are also coupled to frame 104. In some embodiments, the blocks 204 are formed using stamped sheet metal (e.g., aluminum, steel) that is bent into a C-shaped channel that can include apertures or other features that can be used as attachment points for DC power distribution bus bars described in the OCP standard. The blocks 204 can further be used as positioning guides when installing the rear mounting rails 101r and 102r. For example, a surface of blocks 204 can be used as a reference when aligning the rear mounting rails 101r and 102r to the frame 104 in the second configuration. In some embodiments, the blocks 204 are identical components. In some embodiments, the blocks 204 are uniquely designed components. In some embodiments, the features and dimensions of the blocks 204 are defined by an equipment rack standard (e.g., a version of the OCP Open Rack Standard).

Rack 200 includes two horizontal support shelves 206, comprising brackets 206a and 206b (bracket 206b of the lower shelf 206 is not shown in FIG. 2) coupled between the front and rear mounting rails. In some embodiments, IT equipment mounted in rack 200 rests on a horizontal support shelf 206. In some embodiments, the brackets 206a and 206b making up each support shelf 206 are installable without tools, and include protruded features that snap into apertures in each pair of front and rear mounting rails 101 and 102. In some embodiments, the brackets 206a and 206b are coupled to the front and rear mounting rails using threaded hardware. In some embodiments, the shelf 206 can be installed at any position along the length of the rails 101 and 102 in fixed increments of vertical linear distance (e.g., ½ OpenU, 1 OpenU).

OCP-compliant equipment rack 200 further includes vertical and horizontal DC power distribution bus bars 210a and power shelves 210b for housing power distribution units, collectively referred to as OCP power and shelf components 210. In some embodiments, the features and dimensions of the OCP power and shelf components 210 are defined by an equipment rack standard (e.g., a version of the OCP Open Rack Standard).

Figure 3:
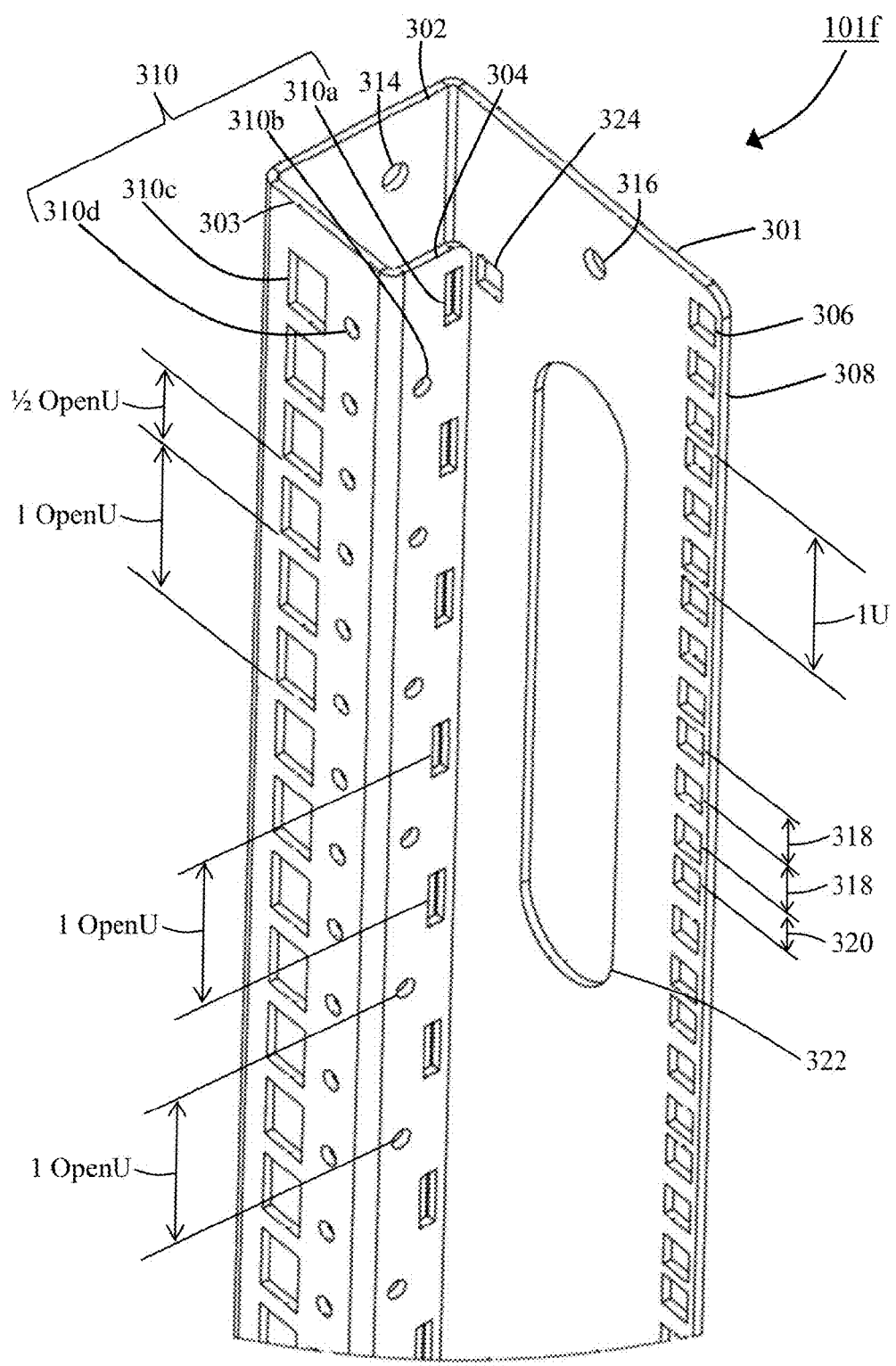
FIG. 3 is a perspective view of a partial exploded diagram of a front IT equipment-mounting rail.

FIG. 3 is a perspective view of a partial exploded diagram of a front mounting rail 101f according to embodiments of this disclosure. Although FIG. 3 is described in reference to the front mounting rail 101f, it should be understood that the front mounting rail 102f includes substantially identical features and dimensions. Rail 101f includes a first plurality of front equipment-mounting apertures 306 disposed substantially adjacent to an outer edge 308 of a first planar surface 301 of the rail 101f. In some embodiments, the apertures 306 are square or rectangular holes. In some embodiments, the apertures 306 are round holes. In some embodiments, the apertures 306 are threaded holes. In some embodiments, the vertical spacing of the apertures 306 is defined as a repeating pattern according to a version of an equipment rack standard (e.g., EIA-310). For example, the vertical spacing of the apertures 306 can be a repeating pattern within a single RU (denoted in FIG. 3 as "1U") of 1.75" encompassing three of the apertures 306, and between adjacent RUs. In some embodiments, the center-to-center vertical spacing 318 of the apertures 306 within a single RU is 0.625" and the center-to-center vertical spacing 320 of the apertures 306 between adjacent RUs is 0.5".

The rail 101f includes a second planar surface 302 that is substantially perpendicular to the first planar surface 301. Surface 302 includes two or more frame-mounting apertures (e.g., 314) for coupling the rail 101f to the frame 104 in the first configuration. In some embodiments, surface 302 has a frame-mounting aperture 314 disposed substantially near each end of rail 101f for coupling rail 101f to top and bottom support members of frame 104. In some embodiments, surface 302 includes one or more additional frame-mounting apertures 314 disposed along surface 302 for coupling rail 101f to a horizontal strut (e.g., 106a, 106b) of frame 104. The frame-mounting apertures can be round holes, square holes, rectangular holes, threaded holes, or any other aperture type configured for coupling an equipment-mounting rail to a frame. The rail 101f can be coupled to the frame 104 through surface 302 using any coupling method known in the art. In one example, nut and bolt hardware are used to couple the rail 101f to the frame 104 through surface 302 utilizing rail-mounting apertures disposed in the frame 104. In another example, a threaded fastener is used to couple the rail 101f to the frame 104 through surface 302 utilizing threaded rail-mounting apertures disposed in the frame 104.

The first planar surface 301 of the front mounting rail 101f has a width sized to align the apertures 306 at a first predefined position defining in part the first equipment-mounting interface 114 when the rail 101f is coupled to the frame 104 through its second planar surface 302. For example, when the rails 101 and 102 are coupled to the frame in the first configuration (e.g., FIG. 1), the surface 301 of the rail 101f is coplanar with the surface 301 of the rail 102f, and the width of the surface 301 aligns the apertures 306 at a position that complies with defined properties the first equipment-mounting interface 114 (e.g., center-to-center horizontal hole spacing between equipment-mounting apertures of the front mounting rails, opening between an outer edge of a surface of the front mounting rails of each pair of mounting rails, front panel width of the IT equipment that can be mounted in the rack 100).

The front mounting rail 101f further includes a third planar surface 303 perpendicular to the second planar surface 302, and a fourth planar surface 304 perpendicular to the third planar surface 303. Rail 101f includes a second plurality of equipment-mounting apertures 310a-310d (collectively referred to as apertures 310) disposed in surfaces 303 and 304. In some embodiments, the apertures 310 comprise four sets of apertures and each set of apertures comprises a different geometric shape and/or aperture type. In some embodiments, the apertures 310 comprises two sets of apertures (e.g., 310c, 310d) disposed in surface 303, and two sets of apertures (e.g., 310a, 310b) disposed in surface 304. In some embodiments, the properties of the apertures 310 (e.g., aperture type, geometric shape, vertical spacing) are defined according to a version of an equipment rack standard such as the OCP Open Rack Standard. For example, the surface 303 can include apertures comprising a rectangular hole 310c and adjacent lanced opening 310d repeated every 48 mm of vertical linear distance. Further, the surface 304 can include apertures comprising an alternating pattern of a rectangular hole 310a repeated every 48 mm of vertical linear distance, and an offset lanced opening 310b repeated every 48 mm of vertical linear distance. In some embodiments, apertures 310c and/or 310d are used for coupling one or more retention components between the front mounting rails 101f and 102f for retaining mounted IT equipment in the rack 200.

The first planar surface 301 includes two or more frame-mounting apertures (e.g., 316) for coupling the rail 101f to the frame 104 in the second configuration. In some embodiments, surface 301 has a frame-mounting aperture 316 disposed substantially near each end of the rail 101f for coupling rail 101f to top and bottom support members of frame 104. In some embodiments, surface 301 includes one or more additional frame-mounting apertures 316 disposed along surface 301 for coupling rail 101f to a horizontal strut (e.g., 106a, 106b) of frame 104. The frame-mounting apertures 316 can be round holes, square holes, rectangular holes, threaded holes, or any other aperture type configured for coupling a mounting rail to a frame. The rail 101f can be coupled to the frame 104 through surface 301 using any coupling method known in the art. In one example, nut and bolt hardware are used to couple the rail 101f to the frame 104 through surface 301 utilizing rail-mounting apertures disposed in the frame 104. In another example, a threaded fastener is used to couple the rail 101f to the frame 104 through surface 301 utilizing threaded rail-mounting apertures disposed in the frame 104.

The second planar surface 302 of the front mounting rail 101f has a second width sized to align the apertures 310 disposed in the third planar surface 303 at a second predefined position defining in part the second equipment-mounting interface 214, and the third planar surface 303 has a third width sized to align the apertures 310 disposed in the surface 304 at a third predefined position defining in part the second equipment-mounting interface 214 when the rail 101f is coupled to the frame 104 through its first planar surface 301. For example, when the mounting rails 101 and 102 are coupled to the frame in the second configuration (e.g., FIG. 2), the surface 302 of the rail 101f is coplanar with the surface 302 of the rail 102f, and the width of the surface 302 positions the surface 303 of rail 101f at a distance from the surface 303 of rail 102f that complies with defined properties of the second equipment-mounting interface 214 (e.g., distance between the front mounting rails). Further, when the mounting rails 101 and 102 are coupled to the frame in the second configuration, the surface 304 of rail 101f is parallel to a surface 404 (FIG. 4) of the rear equipment-mounting rail 101r, and the width of the surface 303 aligns the apertures 310 at a position that complies with defined properties of the second equipment-mounting interface 214 (e.g., horizontal linear distance from the IT equipment-mounting apertures of each front mounting rail to the IT equipment-mounting apertures of its respective rear mounting rail).

Rail 101f can further include utility apertures 322 and 324. In some embodiments, rail 101f includes one or more apertures 322 that are rectangular or oval-shaped openings that can be used as a cable pass-through for routing various cables that are attached to IT equipment mounted in the rack 100 or the rack 200 in an organized fashion. In some embodiments, rail 101f includes one or more apertures 324 for coupling airflow management components (e.g., baffle, plenum) to the front rails 101f and 102f when the rails 101 and 102 are coupled to frame 104 in the first configuration. Apertures 324 can be round holes, square holes, rectangular holes, threaded holes, or any other aperture type configured for coupling airflow management components to rails 101f and 102f.

Figure 4:
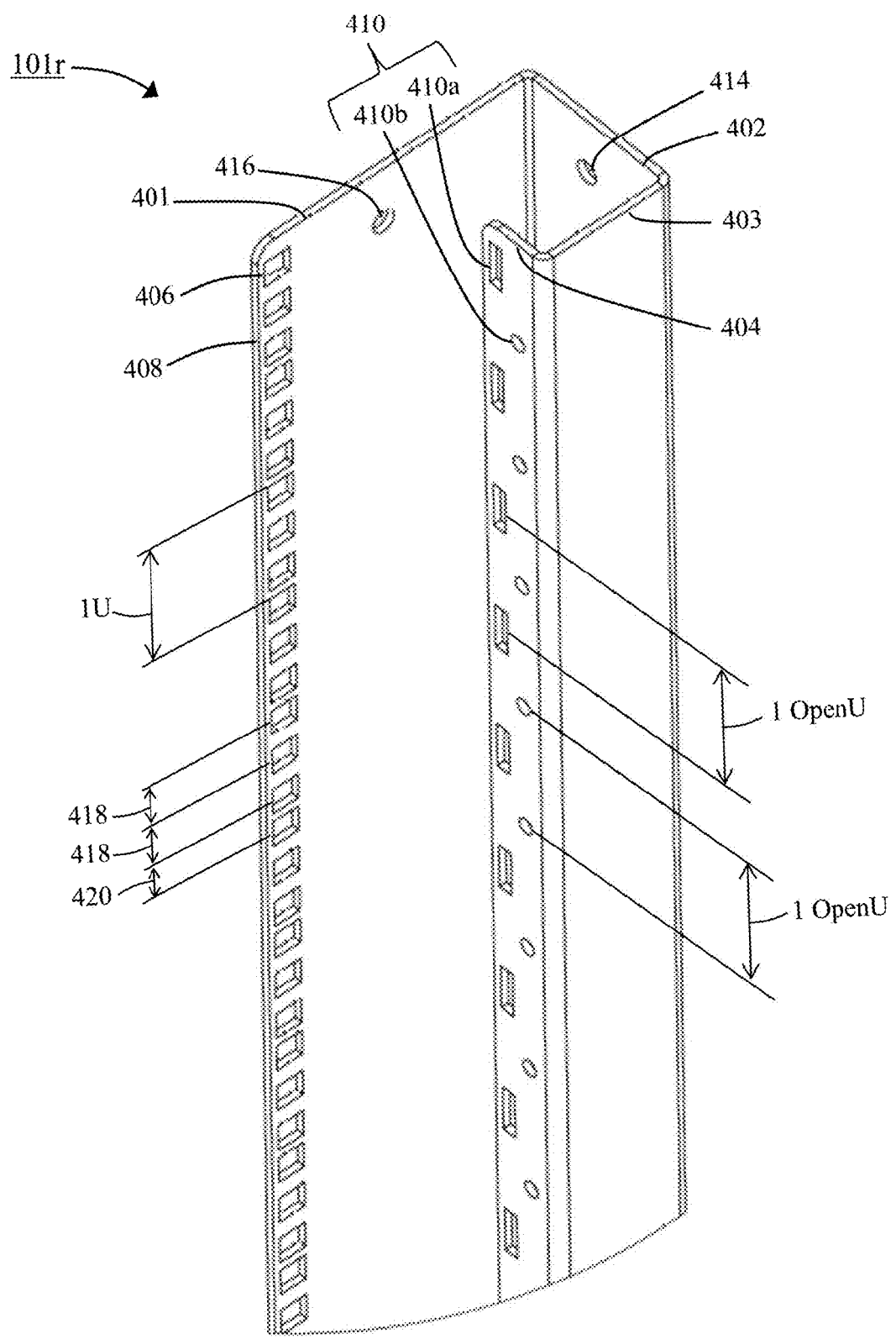
FIG. 4 is a perspective view of a partial exploded diagram of a rear IT equipment-mounting rail.

FIG. 4 is a perspective view of a partial exploded diagram of a rear mounting rail 101r according to embodiments of this disclosure. Although FIG. 4 is described in reference to the rear mounting rail 101r, it should be understood that the rear mounting rail 102r includes substantially identical features and dimensions. Rail 101r includes a first plurality of rear equipment-mounting apertures 406 disposed substantially adjacent to an outer edge 408 of a first planar surface 401 of the rail 101r. In some embodiments, the apertures 406 are square or rectangular holes. In some embodiments, the apertures 406 are round holes. In some embodiments, the apertures 406 are threaded holes. In some embodiments, the vertical spacing of the apertures 406 is defined as a repeating pattern according to a version of an equipment rack standard (e.g., EIA-310). For example, the vertical spacing of the apertures 406 can be a repeating pattern within a single RU (denoted in FIG. 4 as "1U") of 1.75" encompassing three of the apertures 406, and between adjacent RUs. In some embodiments, the center-to-center vertical spacing 418 of the apertures 406 within a single RU is 0.625" and the center-to-center vertical spacing 420 of the apertures 406 between adjacent RUs is 0.5".

The rail 101r includes a second planar surface 402 that is substantially perpendicular to the first planar surface 401. Surface 402 includes two or more frame-mounting apertures (e.g., 414) for coupling the rail 101r to the frame 104 in the first configuration. In some embodiments, surface 402 has a frame-mounting aperture disposed substantially near each end of rail 101r for coupling rail 101r to top and bottom support members of frame 104. In some embodiments, surface 402 includes one or more additional frame-mounting apertures disposed along surface 402 for coupling rail 101r to a horizontal strut (e.g., 106a, 106b) of frame 104. The frame-mounting apertures 414 can be round holes, square holes, rectangular holes, threaded holes, or any other aperture type configured for coupling a mounting rail to a frame. The rail 101r can be coupled to the frame 104 through surface 402 using any coupling method known in the art. In one example, nut and bolt hardware are used to couple the rail 101r to the frame 104 through surface 402 utilizing rail-mounting apertures disposed in the frame 104. In another example, a threaded fastener is used to couple the rail 101r to the frame 104 through surface 402 utilizing threaded rail-mounting apertures disposed in the frame 104.

The first planar surface 401 of the rear mounting rail 101r has a fourth width sized to align the apertures 406 at a fourth predefined position defining in part the first equipment-mounting interface 114 when the rail 101r is coupled to the frame 104 through its second planar surface 402. For example, when the mounting rails 101 and 102 are coupled to the frame 104 in the first configuration (e.g., FIG. 1), the surface 401 of the rail 101r is coplanar with the surface 401 of the rail 101r, and the width of the surface 401 aligns the apertures 406 at a position that complies with defined properties the first equipment-mounting interface 114 (e.g., center-to-center horizontal hole spacing between IT equipment-mounting apertures of the rear mounting rails, opening between an outer edge of a surface of the rear mounting rails).

The rear mounting rail 101r further includes a third planar surface 403 perpendicular to the second planar surface 402, and a fourth planar surface 404 perpendicular to the third planar surface 403. Rail 101r includes a second plurality of equipment-mounting apertures 410a and 410b (collectively referred to as apertures 410) disposed in surface 404. In some embodiments, the apertures 410 comprise two sets of apertures and each set of apertures comprises a different geometric shape and/or aperture type. In some embodiments, the properties of the apertures 410 (e.g., aperture type, geometric shape, vertical spacing) are defined according to a version of an equipment rack standard such as the OCP Open Rack Standard. For example, the surface 404 can include apertures comprising an alternating pattern of a rectangular hole 410a repeated every 48 mm of vertical linear distance, and an offset lanced opening 410b repeated every 48 mm of vertical linear distance.

The first planar surface 401 of the rear mounting rail 101r includes two or more frame-mounting apertures (e.g., 416) for coupling the rail 101r to the frame 104 in the second configuration. In some embodiments, surface 401 has a frame-mounting aperture 416 disposed substantially near each end of rail 101r for coupling rail 101r to top and bottom support members of the frame 104. In some embodiments, surface 401 includes one or more additional frame-mounting apertures 416 disposed along surface 401 for coupling rail 101r to a horizontal strut (e.g., 106a, 106b) of frame 104. The frame-mounting apertures 416 can be round holes, square holes, rectangular holes, threaded holes, or any other aperture type configured for coupling a mounting rail to a frame. The rail 101r can be coupled to the frame 104 through surface 401 using any coupling method known in the art. In one example, nut and bolt hardware are used to couple the rail 101r to the frame 104 through surface 401 utilizing rail-mounting apertures disposed in the frame 104. In another example, a threaded fastener is used to couple the rail 101r to the frame 104 through surface 401 utilizing threaded rail-mounting apertures disposed in the frame 104.

The second planar surface 402 of the rear mounting rail 101r has a fifth width sized to align the third planar surface 403 at a fifth predefined position defining in part the second equipment-mounting interface 214, and the third planar surface 403 has a sixth width sized to align the apertures 410 disposed in the surface 404 at a sixth predefined position defining in part the second equipment-mounting interface 214 when the rail 101r is coupled to the frame 104 through the first planar surface 401 of the rail 101r. For example, when the mounting rails 101 and 102 are coupled to the frame 104 in the second configuration (e.g., FIG. 2), the surface 402 of the rail 101r is coplanar with the surface 402 of the rail 102r, and the width of the surface 402 positions the surface 403 of the rail 101r at a distance from the surface 403 of the rail 102r that complies with defined properties the second equipment-mounting interface 214 (e.g., distance between the front mounting rails of each pair of mounting rails). Further, when the mounting rails 101 and 102 are coupled to the frame 104 in the second configuration, the surface 404 of rail 101r is parallel to a surface 304 (FIG. 3) of the front equipment-mounting rail 101f, and the width of the surface 403 aligns the apertures 410 at a position that complies with defined properties of the second equipment-mounting interface 214 (e.g., horizontal linear distance from the IT equipment-mounting apertures of each front mounting rail to the IT equipment-mounting apertures of its respective rear mounting rail).

In some embodiments, the mounting rails 101 and 102 are formed using sheet metal (e.g., aluminum, steel) that is stamped to add the apertures and other features before being bent using a brake form to create the planar surfaces. In some embodiments, the mounting rails 101 and 102 are formed using an extrusion process, and the apertures and other features are created using a milling process. In some embodiments, the mounting rails 101 and 102 are formed using a cast, mill, or roll form, and the apertures and other features are created using a punch press, laser cutter, water jet, or milling machine. In some embodiments, the widths of the corresponding planar surfaces (e.g., 301 and 401, 302 and 402, 303 and 403, 304 and 404) of the front and rear mounting rails are substantially identical.

Figure 5:
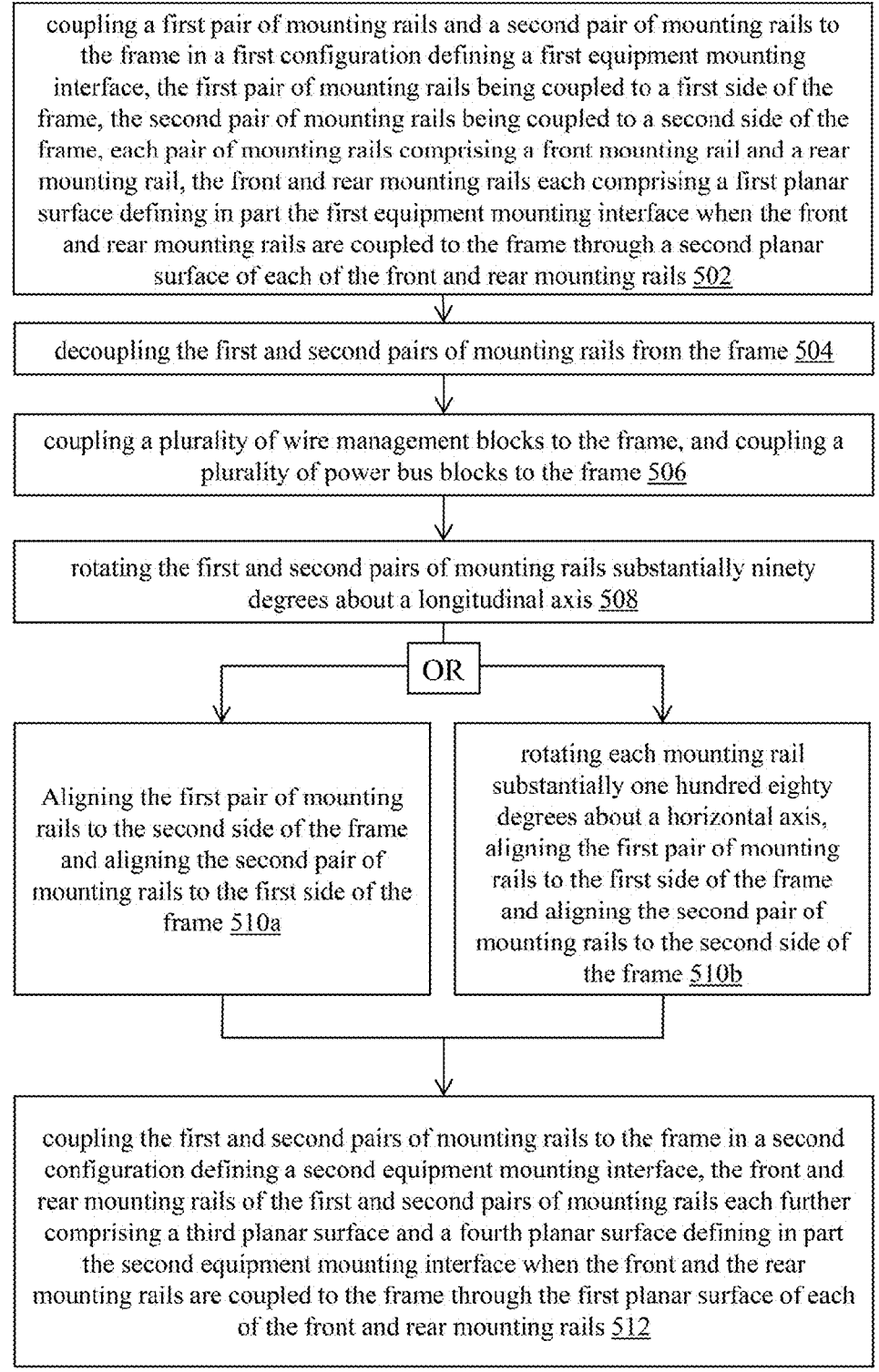
FIG. 5 is a flow diagram of a method for configuring an equipment rack according to embodiments of this disclosure.

FIG. 5 is a flow diagram of a method 500 for configuring an equipment rack comprising a frame utilizing the mounting rails described herein. FIGS. 6A, 6B-1, and 6B-2 each show a diagram corresponding to one or more steps of the method 500. The method 500 can be used, for example, to configure an equipment rack in a first configuration that provides a first equipment-mounting interface that complies with a version of a first standard (e.g., EIA-310), and further to configure an equipment rack in a second configuration that provides a second equipment-mounting interface that complies with a version of a second standard (e.g., OCP Open Rack Standard).

The method 500 includes coupling (502) a first pair of mounting rails 101 and a second pair of mounting rails 102 to the frame in a first configuration defining a first equipment-mounting interface 114, the first pair of mounting rails 101 being coupled to a first side 108a of the frame, the second pair of mounting rails 102 being coupled to a second side 108b of the frame, each pair of mounting rails (101, 102) comprising a front mounting rail (101f, 102f) and a rear mounting rail (101r, 102r), the front and rear mounting rails each comprising a first planar surface (301, 401) defining in part the first equipment-mounting interface 114 when the front and rear mounting rails are coupled to the frame 104 through a second planar surface (302, 402) of each of the front (101f, 102f) and rear (101r, 102r) mounting rails.

FIG. 1, described above, shows an example of a rack 100 including mounting rails 101 and 102 coupled to the frame 104 in the first configuration. Coupling the rails 101 and 102 to the frame 104 can be accomplished by any of the techniques indicated above in the description of the figures (e.g., FIG. 3, FIG. 4).

The method 500 includes decoupling (504) the first pair of mounting rails 101 and the second pair of mounting rails 102 from the frame 104. As shown in diagram 600 of FIG. 6A, rails 101 and 102 have been decoupled from the frame 104. In some embodiments, decoupling includes removing nut and bolt hardware that are used to couple the rails 101 and 102 to the frame 104 through surface 302 utilizing rail-mounting apertures disposed in the frame 104. In some embodiments, decoupling includes removing threaded fasteners that are used to couple the rail 101 and 102 to the frame 104 through surface 302 utilizing threaded rail-mounting apertures disposed in the frame 104.

The method 500 includes coupling (506) a plurality of wire management blocks 202 to the frame 104, each wire management block (202a, 202b) configured to provide a recessed channel for routing one or more wires within and to provide a first alignment surface 602 with which to align one front mounting rail (101f, 102f) in the second configuration, the first alignment surface 602 being a first predetermined distance from a vertical member of the frame 104 adjacent to the front mounting rail (101f, 102f), and coupling a plurality of power bus blocks 204 to the frame 104, each power bus block (204a, 204b) configured to provide a first power bus mounting surface for mounting power bus components (e.g., OCP power and shelf components 210) to the equipment rack 200 and provide a second alignment surface 604 with which to align one rear mounting rail (101r, 102r) in the second configuration, the second alignment surface 604 being a second predetermined distance from a vertical member of the frame 104 adjacent to the rear mounting rail (101r, 102r).

Figure 6A:
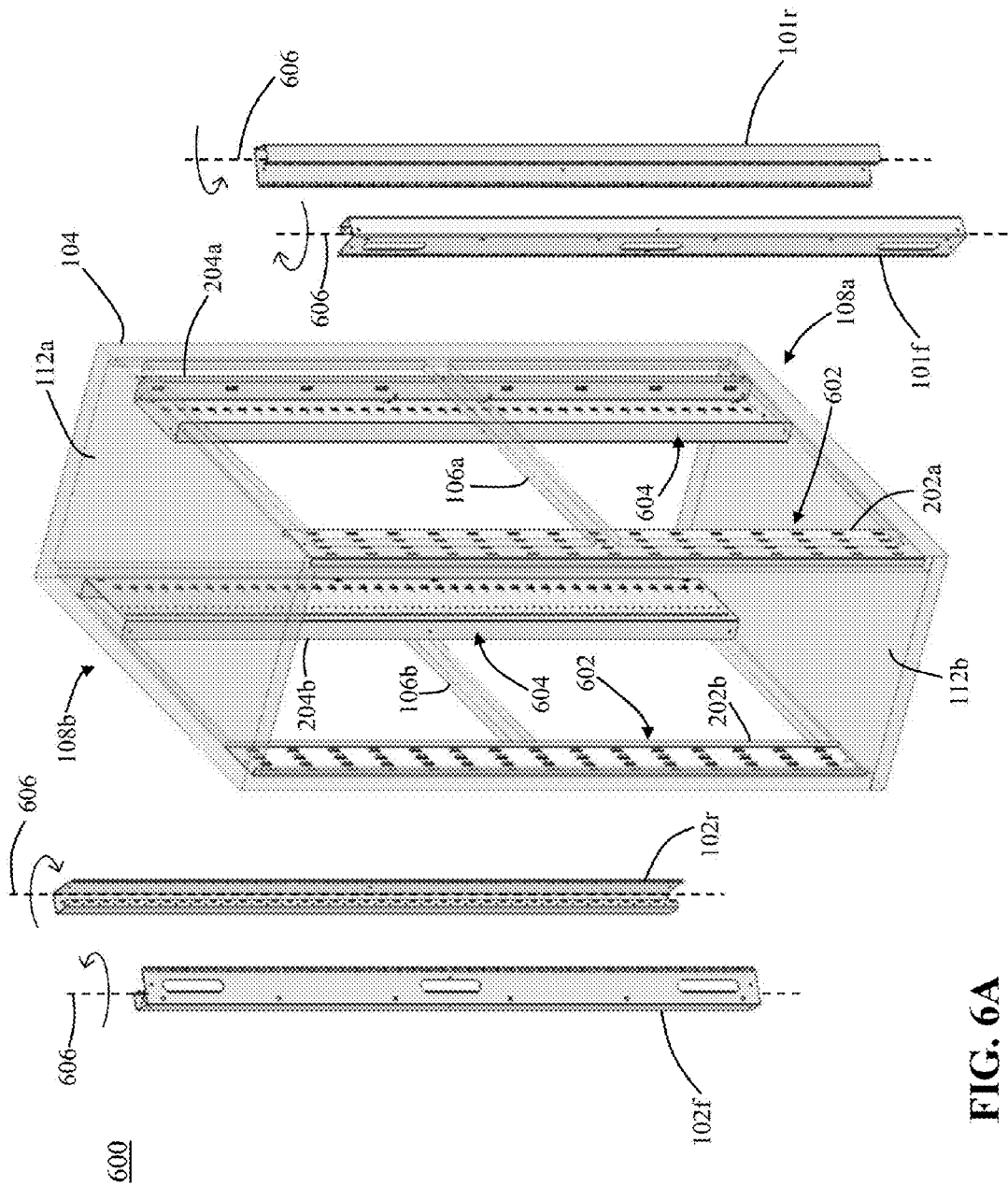

As further shown in diagram 600 of FIG. 6A, wire management blocks 202 and power bus blocks 204 are coupled to the frame 104. The wire management blocks 202 are coupled in the front portion of the frame 104, with the block 202a being coupled to the first side 108a of the frame 104, and the block 202b being coupled to the second side 108b of the frame 104. The power bus blocks 204 are coupled in the rear portion of the frame 104, with the block 204a being coupled to the first side 108a of the frame 104, and the block 204b being coupled to the second side 108b of the frame 104. The blocks 202 and 204 can be coupled to the frame 104 using any coupling method known in the art. In one example, nut and bolt hardware are used to couple the blocks 202 and 204 to the frame 104 through apertures disposed in the blocks 202 and 204, and utilizing rail-mounting apertures disposed in the frame 104. In another example, a threaded fastener is used to couple the blocks 202 and 204 to the frame 104 utilizing threaded rail-mounting apertures disposed in the frame 104.

The method 500 includes rotating (508) the first pair of mounting rails 101 and the second pair of mounting rails 102 substantially ninety degrees about a longitudinal axis 606. Diagram 600 of FIG. 6A shows the rails 101 and 102 each being rotated about a longitudinal axis 606 running vertically down the center of each of the rails 101 and 102, which are shown partially rotated in a direction indicated by the arrow shown proximate to each rail. In some embodiments, the front mounting rail 101f of the first pair of mounting rails 101 and the rear mounting rail 102r of the second pair of mounting rails 102 are rotated in a clockwise direction relative to the longitudinal axis 606. In some embodiments, the front mounting rail 102f of the second pair of mounting rails 102 and the rear mounting rail 101r of the first pair of mounting rails 101 are rotated in a counterclockwise direction relative to the longitudinal axis.

The method 500 can proceed from step 508 to either of step 510a or 510b.

Figures 1, 6B:
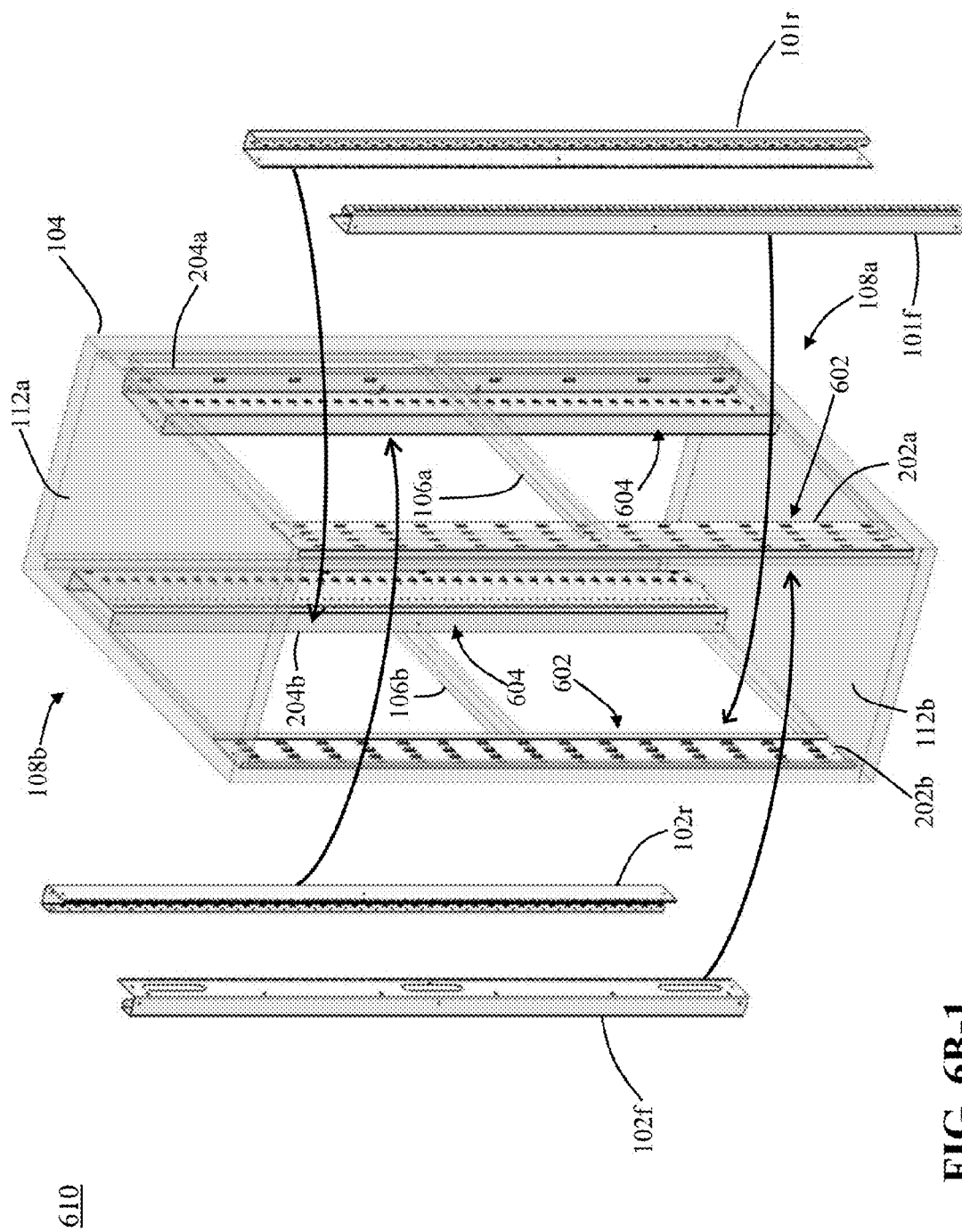
Figures 2, 6B:
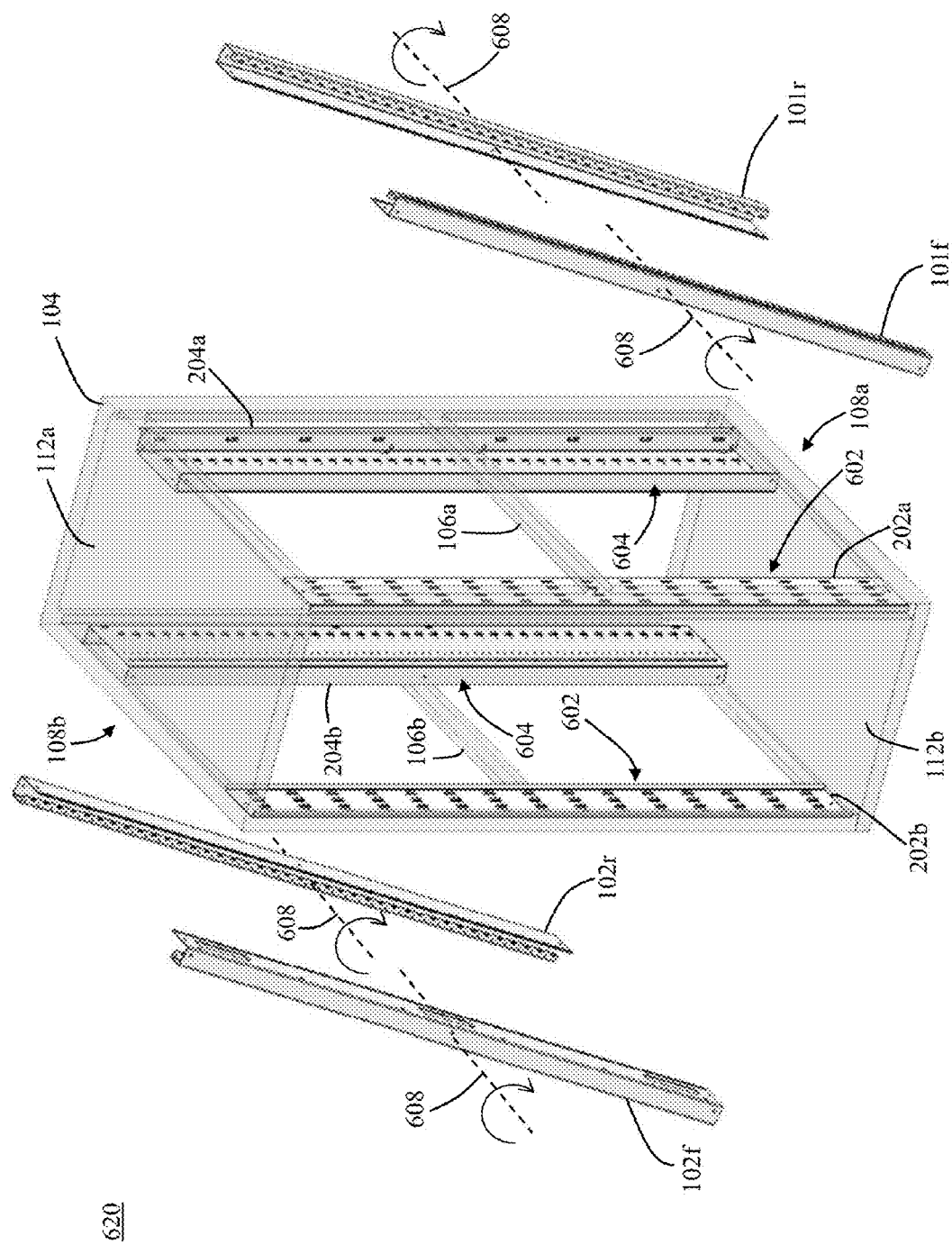

In some embodiments, the method 500 proceeds to step 510a and includes aligning the first pair of mounting rails 101 to the second side of the frame 104 and aligning the second pair of mounting rails 102 to the first side of the frame 104. Diagram 610 of FIG. 6B-1 shows the rails 101 and 102 in their resulting orientation after having been rotated substantially ninety degrees in step 508. An arrow is shown proximate to each of the rails 101 and 102 indicating the side of the frame 104 to which the rails 101 and 102 will be aligned for coupling the rails 101 and 102 to the frame 104 in the second configuration. The rails 101 and 102 are effectively aligned (and subsequently coupled) to the opposite side of the frame 104 from the side that they were coupled to in the first configuration. In some embodiments, the blocks 202 and 204 are used to assist in aligning the pairs of rails 101 and 102. For example, the second planar surface 302 of each of the front mounting rails 101f, 102f can be aligned adjacent to the first alignment surface 602 of each of the plurality of wire management blocks 202. Further, the second planar surface 402 of each the rear mounting rails 101r, 102r can be aligned adjacent to the second alignment surface 604 of each of the plurality of power bus blocks 204.

In some embodiments, the method 500 alternatively proceeds from step 508 to step 510b and includes rotating each mounting rail 101 and 102 substantially one hundred eighty degrees about a horizontal axis 608, aligning the first pair of mounting rails 101 to the first side 108a of the frame 104, and aligning the second pair of mounting rails 102 to the second side 108b of the frame 104. As shown in diagram 620 in FIG. 6B-2, after having been rotated substantially ninety degrees about a longitudinal axis 606 in step 508, the rails 101 and 102 are each rotated about a horizontal axis 608 running through the middle of each of the rails 101 and 102. Each of the rails 101 and 102 in FIG. 6B-2 is shown partially rotated in a direction indicated by the arrow drawn proximate to each rail 101 and 102. After the rails 101 and 102 are rotated one hundred eighty degrees about the horizontal axis 608 (e.g., flipped over, rotated end over end), they are each aligned (and subsequently coupled) to the frame 104. However, unlike step 510a, in step 510b the rails 101 and 102 are aligned to the same side of the frame 104 to which they were coupled in the first configuration. In some embodiments, the blocks 202 and 204 are used to assist in aligning the pairs of rails 101 and 102, as described above with respect to step 510a.

The decision to proceed from step 508 to either of 510a or 510b can be based on features of the pairs of mounting rails 101 and 102. In some embodiments, a label (e.g., adhesive decal, silkscreen) is applied to each of the rails 101 and 102 that includes textual indicators and/or tick marks proximate to the equipment-mounting apertures to assist in aligning and mounting IT equipment in rack 100 or rack 200. In some embodiments, the textual indicators labeling the apertures (e.g., 306 and 310, 406 and 410) of both the first and second configurations are printed in the same orientation, and the method 500 proceeds from step 508 to step 510a so as not to change the orientation of the textual indicators. In some embodiments, the textual indicators labeling the apertures (e.g., 306 and 310, 406 and 410) of both the first and second configurations are printed in different orientations that are rotated one hundred eighty degrees from each other (e.g., upside down relative to each other), and the method 500 proceeds from step 508 to step 510b so as to keep the textual indicators from being upside-down when changing from one configuration to the other.

The method 500 includes coupling (512) the first pair of mounting rails 101 and the second pair of mounting rails 102 to the frame 104 in a second configuration defining a second equipment-mounting interface 214, the front (101f, 102f) and the rear (101r, 102r) mounting rails of the first and second pairs of mounting rails 101 and 102 each further comprising a third planar surface (303, 403) and a fourth planar surface (304, 404) defining in part the second equipment-mounting interface 214 when the front (101f, 102f) and the rear (101r, 102r) mounting rails 101 and 102 are coupled to the frame 104 through the first planar surface (301, 401) of each of the front (101f, 102f) and the rear (101r, 102r) mounting rails. In some embodiments, vertical and horizontal DC power distribution bus bars (e.g., 210a) and power shelves (e.g., 210b) for housing power distribution units can be coupled to the frame 104 at step 512 of method 500. It should be understood that the process of aligning the rails 101 and 102 to the frame 104 described in steps 510a and 510b and the process of coupling the rails 101 and 102 to the frame 104 described in step 512 need not be completed exclusive of one another. In some embodiments, each of the rails 101 and 102 is both aligned and coupled to the frame 104 individually.

FIG. 2, described above, shows an example of a rack 200 including mounting rails 101 and 102 coupled to the frame 104 in the second configuration. Coupling the rails 101 and 102, blocks 202 and 204, and OCP power and shelf components 210 to the frame 104 can be accomplished by any of the techniques indicated above in the description of the figures. It is noted that FIG. 2 shows an example in which the method 500 proceeded through step 510b, as the first pair of mounting rails 101 is coupled to the first side 108a of the frame 104, and the second pair of mounting rails 102 is coupled to the second side 108b of the frame 104.

In some embodiments, the first pair of mounting rails 101 and the second pair of mounting rails 102 are provided as a kit for configuring an equipment rack comprising a frame (e.g., frame 104). In some embodiments, the kit includes the first pair of mounting rails 101 and the second pair of mounting rails 102. In some embodiments, the kit further includes one or more of the wire management blocks 202a and 202b, power bus blocks 204a and 204b, the OCP power and shelf components 203, and horizontal support shelves (e.g., shelf 206). The components provided in the kit can be coupled to a frame in the configurations described herein to provide a first equipment-mounting interface (e.g., 114), or a second equipment-mounting interface (e.g., 214), for mounting IT equipment.

The method 500 as described above proceeded to reconfigure an equipment rack (e.g., rack 100) in a first configuration to an equipment rack (e.g., rack 200) in a second configuration. It should be understood that the method 500 can be used to reconfigure an equipment rack (e.g., rack 200) in a second configuration to an equipment rack (e.g., rack 100) in a first configuration by substantially reversing the steps of method 500.

Comprise, include, and/or plural forms of each are open ended and include the listed parts and can include additional parts that are not listed. And/or is open ended and includes one or more of the listed parts and combinations of the listed parts.

One skilled in the art will realize the embodiments described herein may be embodied in other specific forms without departing from the spirit or essential characteristics thereof. The foregoing embodiments are therefore to be considered in all respects illustrative rather than limiting of the embodiments described herein.

What is claimed is:

1. An equipment rack comprising:
   a frame;
   a first pair of mounting rails and a second pair of mounting rails, each pair of mounting rails comprising:
      a front mounting rail comprising:
         a first plurality of front equipment-mounting apertures being disposed substantially adjacent to an outer edge of a first planar surface of the front mounting rail,
            the first planar surface having a first width sized to align the first plurality of front equipment-mounting apertures at a first predefined position defining in part a first equipment-mounting interface when the front mounting rail is coupled to the frame through a first set of front frame-mounting apertures disposed in a second planar surface of the front mounting rail substantially perpendicular to the first planar surface; and
         a second plurality of front equipment-mounting apertures being disposed in:
            (i) a third planar surface of the front mounting rail substantially perpendicular to the second planar surface, and
            (ii) a fourth planar surface of the front mounting rail surface substantially perpendicular to the third planar surface,
            the second planar surface having a second width sized to align the second plurality of front equipment-mounting apertures disposed in the third planar surface at a second predefined position defining in part a second equipment-mounting interface, and the third planar surface having a third width sized to align the second plurality of front equipment-mounting apertures disposed in the fourth planar surface at a third predefined position defining in part the second equipment-mounting interface when the front mounting rail is coupled to the frame through a second set of front frame-mounting apertures disposed in the first planar surface,
         wherein the first planar surface is directly connected to the second planar surface, the second planar surface is directly connected to the first and third planar surfaces, the third planar surface is directly connected to the second and fourth planar surfaces, and the fourth planar surface is directly connected to the third planar surface; and
      a rear mounting rail comprising:
         a first plurality of rear equipment-mounting apertures being disposed substantially adjacent to an outer edge of a first planar surface of the rear mounting rail,
            the first planar surface having a fourth width sized to align the first plurality of rear equipment-mounting apertures at a fourth predefined position defining in part the first equipment-mounting interface when the rear mounting rail is coupled to the frame through a first set of rear frame-mounting apertures disposed in a second planar surface of the rear mounting rail substantially perpendicular to the first planar surface; and
         a second plurality of rear equipment-mounting apertures being disposed in a fourth planar surface of the rear mounting rail substantially perpendicular to a third planar surface of the rear mounting rail, the third planar surface being substantially perpendicular to the second planar surface,
            the second planar surface having a fifth width sized to align the third planar surface at a fifth predefined position defining in part the second equipment-mounting interface, and the third planar surface having a sixth width sized to align the second plurality of rear equipment-mounting apertures at a sixth predefined position defining in part the second equipment-mounting interface when the rear mounting rail is coupled to the frame through a second set of rear frame-mounting apertures disposed in the first planar surface,
         wherein the first planar surface is directly connected to the second planar surface, the second planar surface is directly connected to the first and third planar surfaces, the third planar surface is directly connected to the second and fourth planar surfaces, and the fourth planar surface is directly connected to the third planar surface;

wherein the first equipment-mounting interface is defined by a first configuration of the first and second pairs of mounting rails; and wherein the second equipment-mounting interface is defined by a second configuration of the first and second pairs of mounting rail.

2. The equipment rack of claim 1 wherein the first equipment-mounting interface complies with a first equipment rack standard specifying an equipment rack for mounting equipment having a first front panel width, the first front panel width being substantially 19 inches.

3. The equipment rack of claim 2 wherein the first equipment rack standard is a version of Electronic Industries Alliance 310 (EIA-310).

4. The equipment rack of claim 1 wherein the second equipment-mounting interface complies with a second equipment-mounting standard specifying an equipment rack for mounting equipment having a first enclosure width, the first enclosure width being substantially 538 millimeters.

5. The equipment rack of claim 4 wherein the second equipment rack standard is a version of an Open Compute Project Open Rack standard.

6. The equipment rack of claim 1 wherein the first and second pairs of mounting rails in the first configuration are rotated substantially ninety degrees about a longitudinal axis in the second configuration.

7. The equipment rack of claim 1 wherein the first pair of mounting rails is coupled to a first side of the frame in the first configuration and the second pair of mounting rails is coupled to a second side of the frame in the first configuration.

8. The equipment rack of claim 7 wherein the first pair of mounting rails is coupled to the second side of the frame in the second configuration and the second pair of mounting rails is coupled to the first side of the frame in the second configuration.

9. The equipment rack of claim 1 wherein the first and second pairs of mounting rails in the first configuration are each rotated substantially one hundred eighty degrees about a horizontal axis in the second configuration.

10. The equipment rack of claim 9 wherein the first pair of mounting rails is coupled to a first side of the frame in the second configuration and the second pair of mounting rails is coupled to a second side of the frame in the second configuration.

11. The equipment rack of claim 1 further comprising:

a plurality of wire management blocks for coupling to the frame when the first and second pairs of mounting rails are in the second configuration, each wire management block configured to:

provide a recessed channel for routing one or more wires within; and provide a first alignment surface with which to align one front mounting rail, the first alignment surface being a first predetermined distance from a vertical member of the frame adjacent to the front mounting rail; and a plurality of power bus blocks for coupling to the frame when the first and second pairs of mounting rails are in the second configuration, each power bus block configured to:

provide a first power bus mounting surface for mounting power bus components in the equipment rack; and provide a second alignment surface with which to align one rear mounting rail, the second alignment surface being a second predetermined distance from a vertical member of the frame adjacent to the rear mounting rail.

12. A kit for configuring an equipment rack comprising a frame, the kit comprising:

a first pair of mounting rails and a second pair of mounting rails, each pair of mounting rails comprising:

a front mounting rail comprising:

a first plurality of front equipment-mounting apertures being disposed substantially adjacent to an outer edge of a first planar surface of the front mounting rail, the first planar surface having a first width sized to align the first plurality of front equipment-mounting apertures at a first predefined position defining in part a first equipment-mounting interface when the front mounting rail is coupled to the frame through a first set of front frame-mounting apertures disposed in a second planar surface of the front mounting rail substantially perpendicular to the first planar surface; and a second plurality of front equipment-mounting apertures being disposed in:

(i) a third planar surface of the front mounting rail substantially perpendicular to the second planar surface, and (ii) a fourth planar surface of the front mounting rail surface substantially perpendicular to the third planar surface, the second planar surface having a second width sized to align the second plurality of front equipment-mounting apertures disposed in the third planar surface at a second predefined position defining in part a second equipment-mounting interface, and the third planar surface having a third width sized to align the second plurality of front equipment-mounting apertures disposed in the fourth planar surface at a third predefined position defining in part the second equipment-mounting interface when the front mounting rail is coupled to the frame through a second set of front frame-mounting apertures disposed in the first planar surface, wherein the first planar surface is directly connected to the second planar surface, the second planar surface is directly connected to the first and third planar surfaces, the third planar surface is directly connected to the second and fourth planar surfaces, and the fourth planar surface is directly connected to the third planar surface; and a rear mounting rail comprising:

a first plurality of rear equipment-mounting apertures being disposed substantially adjacent to an outer edge of a first planar surface of the rear mounting rail, the first planar surface having a fourth width sized to align the first plurality of rear equipment-mounting apertures at a fourth predefined position defining in part the first equipment-mounting interface when the rear mounting rail is coupled to the frame through a first set of rear frame-mounting apertures disposed in a second planar surface of the rear mounting rail substantially perpendicular to the first planar surface; and a second plurality of rear equipment-mounting apertures being disposed in:
(i) a fourth planar surface of the rear mounting rail substantially perpendicular to a third planar surface of the rear mounting rail, the third planar surface being substantially perpendicular to the second planar surface,
the second planar surface having a fifth width sized to align the third planar surface at a fifth predefined position defining in part the second equipment-mounting interface, and the third planar surface having a sixth width sized to align the second plurality of rear equipment-mounting apertures at a sixth predefined position defining in part the second equipment-mounting interface when the rear mounting rail is coupled to the frame through a second set of rear frame-mounting apertures disposed in the first planar surface,
wherein the first planar surface is directly connected to the second planar surface, the second planar surface is directly connected to the first and third planar surfaces, the third planar surface is directly connected to the second and fourth planar surfaces, and the fourth planar surface is directly connected to the third planar surface;
wherein the first equipment-mounting interface is defined by a first configuration of the first and second pairs of mounting rails; and
wherein the second equipment-mounting interface is defined by a second configuration of the first and second pairs of mounting rail.

13. The kit of claim 12 wherein the first equipment-mounting interface complies with a first equipment rack standard specifying an equipment rack for mounting equipment having a first front panel width, the first front panel width being substantially 19 inches.

14. The kit of claim 13 wherein the first equipment rack standard is a version of Electronic Industries Alliance 310 (EIA-310).

15. The kit of claim 12 wherein the second equipment-mounting interface complies with a second equipment-mounting standard specifying an equipment rack for mounting equipment having a first enclosure width, the first enclosure width being substantially 538 millimeters.

16. The kit of claim 15 wherein the second equipment rack standard is a version of an Open Compute Project Open Rack standard.

17. The kit of claim 12 wherein the first and second pairs of mounting rails in the first configuration are rotated substantially ninety degrees about a longitudinal axis in the second configuration.

18. The kit of claim 12 wherein the first pair of mounting rails is coupled to a first side of the frame in the first configuration and the second pair of mounting rails is coupled to a second side of the frame in the first configuration.

19. The kit of claim 18 wherein the first pair of mounting rails is coupled to the second side of the frame in the second configuration and the second pair of mounting rails is coupled to the first side of the frame in the second configuration.

20. The kit of claim 12 wherein the first and second pairs of mounting rails in the first configuration are each rotated substantially one hundred eighty degrees about a horizontal axis in the second configuration.

21. The kit of claim 20 wherein the first pair of mounting rails is coupled to a first side of the frame in the second configuration and the second pair of mounting rails is coupled to a second side of the frame in the second configuration.

22. The kit of claim 12 further comprising:
a plurality of wire management blocks for coupling to the frame when the first and second pairs of mounting rails are in the second configuration, each wire management block configured to:
provide a recessed channel for routing one or more wires within; and
provide a first alignment surface with which to align one front mounting rail, the first alignment surface being a first predetermined distance from a vertical member of the frame adjacent to the front mounting rail; and
a plurality of power bus blocks for coupling to the frame when the first and second pairs of mounting rails are in the second configuration, each power bus block configured to:
provide a first power bus mounting surface for mounting power bus components to the equipment rack; and
provide a second alignment surface with which to align one rear mounting rail, the second alignment surface being a second predetermined distance from a vertical member of the frame adjacent to the rear mounting rail.

23. A method for configuring an equipment rack comprising a frame, the method comprising:
coupling a first pair of mounting rails and a second pair of mounting rails to the frame in a first configuration defining a first equipment-mounting interface, the first pair of mounting rails being coupled to a first side of the frame, the second pair of mounting rails being coupled to a second side of the frame, each pair of mounting rails comprising a front mounting rail and a rear mounting rail, the front and rear mounting rails each comprising a first planar surface defining in part the first equipment-mounting interface when the front and rear mounting rails are coupled to the frame through a second planar surface of each of the front and rear mounting rails;
decoupling the first and second pairs of mounting rails from the frame;
rotating the first and second pairs of mounting rails substantially ninety degrees about a longitudinal axis; and
coupling the first and second pairs of mounting rails to the frame in a second configuration defining a second equipment-mounting interface, the front and rear mounting rails of the first and second pairs of mounting rails each further comprising a third planar surface and a fourth planar surface defining in part the second equipment-mounting interface when the front and the rear mounting rails are coupled to the frame through the first planar surface of each of the front and rear mounting rails,
wherein the first equipment-mounting interface comprises:
a first linear distance between outer edges of the first planar surfaces of the front mounting rails and a second linear distance between outer edges of the first planar surfaces of the rear mounting rails, the first and second linear distances sized for mounting equipment having a first width; and
wherein the second equipment-mounting interface comprises one or more of:
a third linear distance between the third planar surfaces of the front mounting rails and a fourth linear distance between the third planar surfaces of the rear mounting rails, the third and fourth linear distances sized for mounting equipment having a second width.

24. The method of claim 23 wherein coupling the first and second pairs of mounting rails to the frame in the second configuration further comprises:

aligning the first pair of mounting rails to the second side of the frame; and
aligning the second pair of mounting rails to the first side of the frame.

25. The method of claim 23 wherein coupling the first and second pairs of mounting rails to the frame in the second configuration further comprises:
  rotating each mounting rail substantially one hundred eighty degrees about a horizontal axis
  aligning the first pair of mounting rails to the first side of the frame; and
  aligning the second pair of mounting rails to the second side of the frame.

26. The method of claim 23 further comprising:
  coupling a plurality of wire management blocks to the frame, each wire management block configured to:
    provide a recessed channel for routing one or more wires within; and
    provide a first alignment surface with which to align one front mounting rail in the second configuration, the first alignment surface being a first predetermined distance from a vertical member of the frame adjacent to the front mounting rail; and
  coupling a plurality of power bus blocks to the frame, each power bus block configured to:
    provide a first power bus mounting surface for mounting power bus components to the equipment rack; and
    provide a second alignment surface with which to align one rear mounting rail in the second configuration, the second alignment surface being a second predetermined distance from a vertical member of the frame adjacent to the rear mounting rail.

27. The method of claim 26 wherein coupling the first and second pairs of mounting rails to the frame in the second configuration further comprises:
  aligning the second planar surfaces of the front mounting rails adjacent to the first alignment surfaces of the plurality of wire management blocks; and
  aligning the second planar surfaces of the rear mounting rails adjacent to the second alignment surfaces of the plurality of power bus blocks.

28. The method of claim 23 wherein rotating further comprises:
  rotating the front mounting rail of the first pair of mounting rails and the rear mounting rail of the second pair of mounting rails in a clockwise direction relative to the longitudinal axis; and
  rotating the front mounting rail of the second pair of mounting rails and the rear mounting rail of the first pair of mounting rails in a counterclockwise direction relative to the longitudinal axis.

29. The method of claim 23, wherein the first equipment-mounting interface further comprises a first plurality of front equipment-mounting apertures disposed in the first planar surfaces of the front mounting rails and a first plurality of rear equipment-mounting apertures disposed in the first planar surfaces of the rear mounting rails, the first plurality of front equipment-mounting apertures and first plurality of rear equipment-mounting apertures aligned at a first predefined position, for mounting equipment having a first mounting hole pattern; and
  wherein the second equipment-mounting interface further comprises a second plurality of front equipment-mounting apertures disposed in the third and fourth planar surfaces of the front mounting rails and a second plurality of rear equipment-mounting apertures disposed in the fourth planar surfaces of the rear mounting rails, the second plurality of front equipment-mounting apertures and second plurality of rear equipment-mounting apertures aligned at a second predefined position for mounting equipment having a second mounting hole pattern.

30. The method of claim 29, wherein the first and second linear distances are substantially the same as the third and fourth linear distances.

\* \* \* \* \*